United States Patent [19]

Rebrovic

[11] Patent Number: 5,399,749
[45] Date of Patent: Mar. 21, 1995

[54] CATALYZED PROCESS FOR OXIDATION OF OZONIDES OF UNSATURATES TO CARBOXYLIC ACIDS

[75] Inventor: Louis Rebrovic, Cincinnati, Ohio

[73] Assignee: Henkel Corporation, Plymouth Meeting, Pa.

[21] Appl. No.: 768,287

[22] PCT Filed: Sep. 9, 1991

[86] PCT No.: PCT/US91/06449
§ 371 Date: Sep. 9, 1991
§ 102(e) Date: Sep. 9, 1991

[87] PCT Pub. No.: WO93/05007
PCT Pub. Date: Mar. 18, 1993

[51] Int. Cl.⁶ .............................................. C07C 51/16
[52] U.S. Cl. ................................................... 562/544
[58] Field of Search ................................. 562/542, 544

[56] References Cited

U.S. PATENT DOCUMENTS

| | | | |
|---|---|---|---|
| 3,026,353 | 3/1962 | Frank et al. | 562/528 |
| 3,868,392 | 2/1975 | Siclari et al. | 562/544 |
| 3,979,450 | 7/1976 | Jamison et al. | 318/150 |
| 4,287,130 | 9/1981 | Dohm et al. | 562/544 |
| 4,940,808 | 7/1990 | Schulz et al. | 562/544 |
| 5,023,066 | 6/1991 | Gimpel et al. | 423/328 |

FOREIGN PATENT DOCUMENTS

| | | |
|---|---|---|
| 203632 | 9/1986 | European Pat. Off. |
| 0295471 | 12/1988 | European Pat. Off. |
| 3222143 | 7/1982 | Germany |
| 772410 | 12/1955 | United Kingdom |
| 330154 | 4/1972 | U.S.S.R. |

*Primary Examiner*—Arthur C. Prescott
*Attorney, Agent, or Firm*—Ernest G. Szoke; Wayne C. Jaeschke; Norvell E. Wisdom, Jr.

[57] ABSTRACT

Zeolites, particularly X type zeolites, essentially irrespective of the cation they contain, are effective heterogeneous catalysts for the oxidative conversion of the products of reaction of organic molecules containing a —HC=CH— structure with ozone to at least two carboxylic acid molecules, with gaseous diatomic oxygen as the oxidative agent. The process is particularly well adapted to converting oleic acid into a mixture of azelaic and pelargonic acids.

20 Claims, 3 Drawing Sheets

CATALYZED PROCESS FOR OXIDATION OF OZONIDES OF UNSATURATES TO CARBOXYLIC ACIDS

FIELD OF THE INVENTION

This invention relates processes for making carboxylic acids by treating alkenes and other organic compounds containing carbon-carbon double bonds with ozone to form ozonides and oxidizing the ozonides to form a carboxyl group on each carbon atom in the original carbon-carbon double bond. The oxidation step utilizes diatomic oxygen, which may be mixed with other gases, as oxidant and is speeded by use of a heterogeneous catalyst.

STATEMENT OF RELATED ART

The general chemical course of the reactions involved in a process according to this invention is well known. The part of the overall process involving oxidation of ozonides has been reported to be catalyzed with "Lindlar Catalyst", which is a special preparation of palladium on calcium carbonate, selenium oxide, metal soaps, ester soaps, manganese diacetate, a cation exchange resin catalyst, and salts of metals with two or more stable valence states (in addition to zero valence).

In what is believed to be one of the examples of this related art most pertinent to the present invention, U.S. Pat. No. 3,979,450 according to an abstract thereof teaches making dicarboxylic acids by ozonizing a cycloolefin dissolved in a lower monocarboxylic acid, treating the resulting product with aqueous hydrogen peroxide, passing the resulting mixture through a solid acid catalyst at 30°–60° C., completing the oxidation in a separate reaction zone at 50°–80° C. in the absence of catalyst, and decomposing the oxidation product by heating at 90°–110° C.

U.S.S.R. patent publication 330154 according to an abstract thereof teaches ozonizing oleic acid in solution in a lower carboxylic acid, then passing the ozonilysate and hydrogen peroxide through a column of solid, acidic catalyst at 50°–80 C. to produce azelaic and pelargonic acids.

Catalysis of the decomposition of hydroperoxides by zeolites and clays has been reported, but the type of decomposition reported is not believed to lead to carboxylic acid products. For example, published European Patent Application 0 203 632 according to an abstract thereof teaches that crystalline zeolites in which a portion of the silicon atoms in the crystal lattice are replaced by aluminum and boron atoms are effective catalysts for the selective decomposition of cumene hydroperoxide to phenol and acetone; and published German Patent Application DE 32 22 143 according to an abstract thereof teaches that NaA, NaX, and NaY zeolites modified with cobalt catalyze the decomposition of cyclohexyl hydroperoxide to cyclohexanone and cyclohexanol. These hydroperoxides are distinct chemical entities from ozonides, however.

DESCRIPTION OF THE INVENTION

In this description, except in the claims and the operating examples or where explicitly otherwise indicated, all numbers describing amounts of ingredients or reaction conditions are to be understood as modified by the word "about" in describing the broadest embodiments of the invention. Operation within the exact numerical limits given is generally preferred.

SUMMARY OF THE INVENTION

A major embodiment of the present invention is a process in which organic molecules containing a structural unit of the formula —CH═CH— are each converted into two or more molecules containing a structural unit of the formula —COOH by reaction with ozone to form one or more ozonides and subsequent or simultaneous reaction of the ozonide(s) with gaseous diatomic oxygen. (In this description, any oxygen containing product of direct reaction between ozone and organic molecules containing carbon-carbon double bonds is to be understood as an ozonide.) The diatomic oxygen may be mixed with other non-oxidizing gases, as in normal air or oxygen enriched air. The improvement in the process is that the reagents are in fluid form and are in contact, during at least part of the reaction with the diatomic oxygen gas, with a solid phase selected from X and Y type zeolites, preferably X type zeolites, most preferably sodium or potassium zeolite X. (An X type zeolite has the general crystal structure of faujasite and an atomic ratio of silicon to aluminum atoms in the range from 1 to 1.5; a Y type zeolite is otherwise similar but has an atomic ratio of silicon to aluminum atoms in the range from >1.5 to 3.) The zeolite serves as a heterogeneous catalyst to speed the reaction toward formation of carboxylic acids.

BRIEF DESCRIPTION OF THE DRAWINGS

All of the drawings show kinetics according to one or more processes according to this invention and/or according to comparison examples from prior art.

DESCRIPTION OF THE PREFERRED EMBODIMENTS

Figure 1:
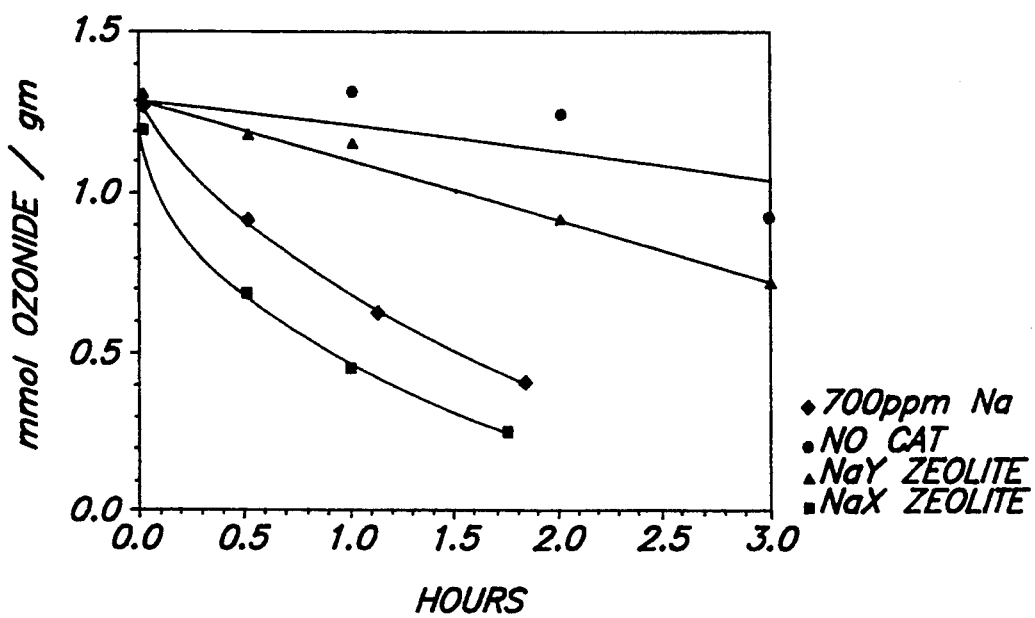

Except for the use of this heterogeneous catalyst, a process according to the invention may be performed with conventional reagents and reaction conditions. For example, the unsaturated organic molecules to be converted to carboxylic acids and/or the ozonides formed from them may be dissolved in a convenient solvent to facilitate reaction. Otherwise saturated carboxylic acids and mixtures thereof, which may contain straight and/or branched alkyl groups attached to the carboxyl groups, are generally the preferred solvents for the process. The initial concentration of unsaturated molecules in the liquid mixture treated with ozone when a solvent is used is preferably from 5 to 95 percent by weight (hereinafter "w/o"), or with increasing preference from 30 to 70 or from 50 to 80 w/o.

The ozone used may be, and preferably is, mixed with diatomic oxygen and/or non reactive gases such as nitrogen during its mixing with a fluid containing unsaturated molecules as part of a process according to this invention. With increasing preference, the gas mixture supplied for reaction contains from 0.5 to 14, from 1 to 8, or from 2 to 6 volume percent (hereinafter "v/o") of ozone; and, independently, with increasing preference, the same gas mixture contains from 99.5 to 86, from 99 to 92, or from 98 to 94 v/o of diatomic oxygen. Preferably the fluid containing the unsaturated molecules to be converted to carboxylic acids is a liquid and is mixed with the gas containing ozone by some means for promoting efficient contact; such means are generally known in the art.

With increasing preference, the temperature of the reagents during the reaction of ozone with unsaturated molecules in a process according to this invention is from 17° to 45°, from 20° to 40°, or from 23° to 30°C.

If the gas mixture containing ozone also contains diatomic oxygen, a process according to this invention can be completed in a single step. Normally, however, it is more efficient to separate the process into two steps: formation of the ozonides and subsequent oxidative decomposition of the ozonides to carboxylic acids. If the process is performed in two steps, it is generally preferred to use a solvent in the second step as well as the first, and the same type of solvent, i.e., otherwise saturated carboxylic acids or mixtures thereof, and the same concentrations as noted above, but referred to ozonides rather than to the molecules containing unsaturation, are preferred.

If the process is performed in two steps, with increasing preference, the temperature of the reagents during the reaction of ozonides with an diatomic oxygen gas in a process according to this invention is from 50° to 110°, from 50° to 90°, or from 60° to 80°, C.

The relative amounts of fluid reagents and solid catalyst in a process according to this invention can be varied within wide limits. If the catalyst is used in finely divided form and continuously stirred with the fluid reagents during reaction throughout a volume that includes all the ozonides being oxidized in a batch process, as is preferred in one embodiment of the invention, the amount of catalyst used should be, with increasing preference, from 0.1 to 50, from 0.5 to 25, or from 1 to 16, w/o of the amount of the total of—CH=CH— groups and/or ozonides thereof present in the fluid reaction mixture that is mixed together with the finely divided catalyst. In another embodiment, preferred for large scale operations, the catalyst is used in a fixed bed through which the fluid reaction mixture containing ozonides is passed. In this embodiment, the amount of catalyst used is, with increasing preference, from 1 to 250, from 50 to 200, or from 75 to 150, w/o of the amount of the total of—CH=CH—groups and/or ozonides thereof present in the amount of fluid reaction mixture passed through the fixed bed in one hour.

A particularly preferred unsaturated starting material for the process is oleic acid, either relatively pure or in a technical mixture, usually derived from natural fats or oils, that is nominally oleic acid but may contain as little as 65 w/o of pure oleic acid along with various other saturated and unsaturated acids with carbon chain lengths of $C_{10-20}$.

The practice of the invention can be further appreciated with the help of the following working examples and comparison examples.

EXAMPLE AND COMPARISON EXAMPLE GROUP 1

A mixture of 50 w/o of each of "pure" (99 w/o) oleic acid and hexanoic acid was treated with a gas containing 5 v/o of ozone with the balance $O_2$ at a rate to supply 0.00644 millimole (hereinafter "mmole") of $O_3$ per mmole of oleic acid present in the acid mixture per minute for 2.5–3.0 hours at 23°–25° C. The gas was supplied through a conventional sparger with a pore size of 147–174 micrometers (hereinafter "μm"). Afterwards, nitrogen gas was sparged into the post-reaction mixture for 15 minutes, in order to free the mixture substantially from either form of gaseous oxygen. The mixture thereby formed can be used immediately or safely stored at −20° C. for later use.

An amount of 23 grams (hereinafter "g") of a mixture prepared as described above was placed together with 0.30 g of catalyst if zeolite was used, an amount of sodium acetate to give 700 parts per million by weight (hereinafter "ppm") in the reaction mixture, or in one comparison example, no catalyst, into a container permitting rapid stirring to maintain circulation of the solid catalyst if used and gas sparging. Three different catalysts were used: sodium acetate (according to prior art), Na-Y Zeolite (commercial product available from UOP, Inc., Tarrytown, New York, USA; a catalyst within the broad embodiment of this invention), and Na-X Zeolite (same commercial source as for Na-Y Zeolite; a catalyst within the preferred embodiment of this invention.)

The container was placed in a temperature controlled water bath and initially sparged with nitrogen while the temperature was maintained 10° below the desired reaction temperature of 60° C. The temperature controller for the water bath was then set to increase the temperature up to the desired reaction temperature. When the temperature of the water bath reached a value 5° below the desired reaction temperature, a sample of the reaction mixture contents was taken and labelled as time zero. When the desired reaction temperature was reached in the water bath, the gas flow was changed from nitrogen to oxygen at a rate of 350 milliliters per minute (hereinafter "mL/min") and timing of the reaction was begun. Samples were taken at various intervals and analyzed for ozonide content, with results shown in FIG. 1. After a reaction time corresponding to the abscissa of the last data point shown in FIG. 1, the chain length distribution of the carboxylic acids in the product mixture was measured, with results shown in Table 1.

As may be seen from FIG. 1, the Na-X Zeolite catalyzed process according to the invention decomposed ozonide at a slightly faster rate than sodium acetate, and the amounts of the desired azelaic and pelargonic acid products were substantially the same as shown in Table 1. The Na-Y Zeolite catalyst was not nearly as good as Na-X but still better than no catalyst at all.

TABLE 1

PRODUCT ANALYSIS FOR EXAMPLE AND COMPARISON EXAMPLE GROUP 1

| Acid Name | Weight Percent of Acid in Product When Using: | | | |
|---|---|---|---|---|
| | No Catalyst | 700 ppm Na | Na—Y Zeolite | Na—X Zeolite |
| Pentanoic | 0.141 | 0.172 | 0.146 | 0.163 |
| Hexanoic | 42.434 | 41.940 | 41.130 | 42.321 |
| Octanoic | <0.06 | 0.113 | <0.07 | <0.01 |
| Pelargonic | 9.126 | 19.413 | 11.985 | 19.098 |
| Decanoic | 2.146 | 0.702 | 1.911 | 0.482 |
| Adipic | 0.271 | 0.285 | 0.102 | 0.268 |
| Suberic | 0.942 | 0.607 | 1.252 | 0.295 |
| Azelaic | 11.472 | 21.770 | 14.907 | 23.120 |

Note for Table 1
The "Product" includes the hexanoic acid originally added as solvent.

EXAMPLE AND COMPARISON EXAMPLE GROUP 2

Figure 2A:
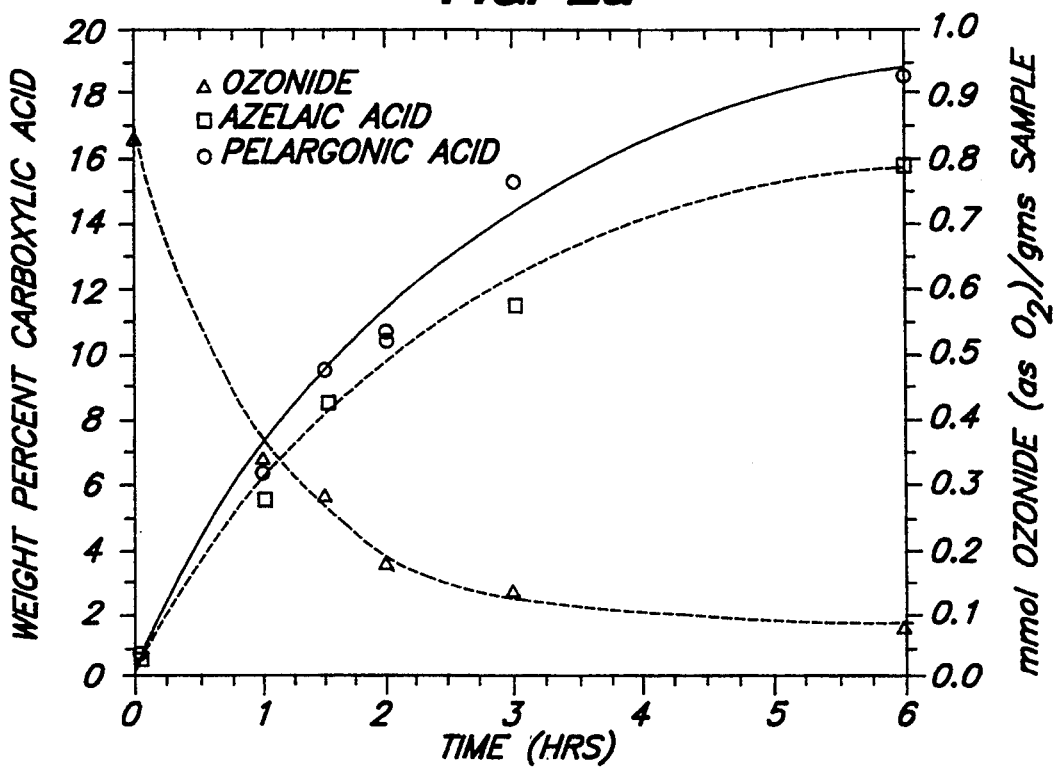
Figure 2B:
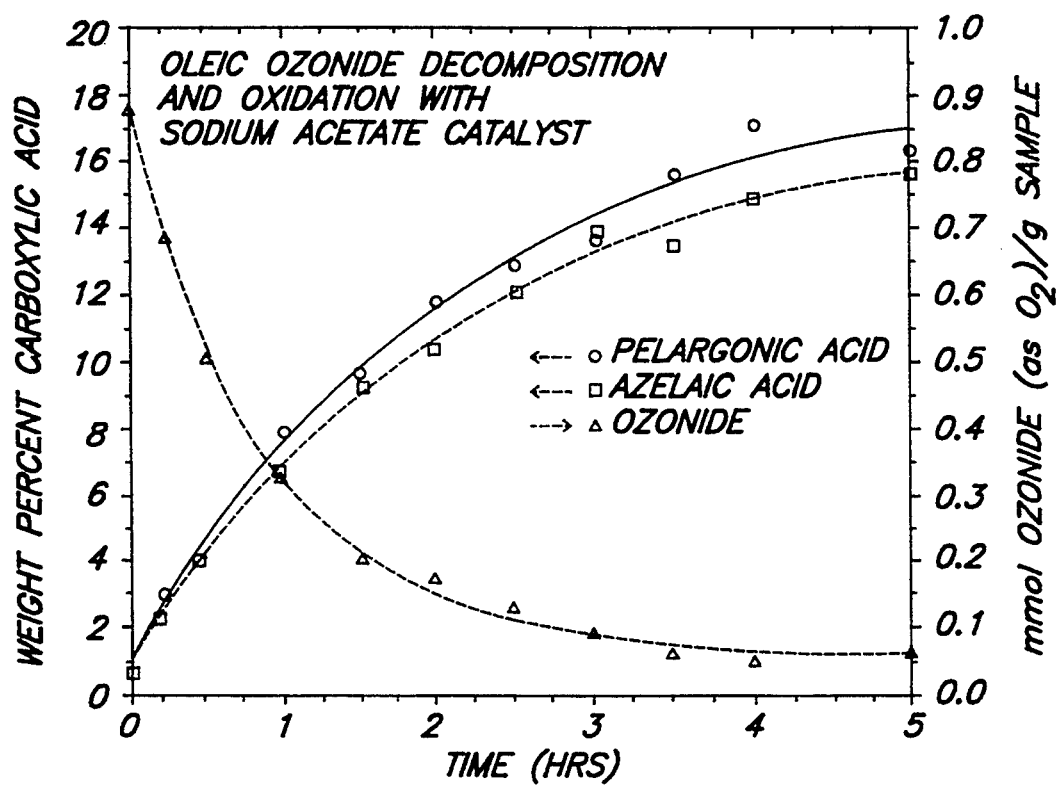

This was performed in the same manner as for Example 1, except that (i) only Na-X Zeolite and sodium acetate catalysts were used; (ii) the ozonide was prepared from a solution of 10.0 gm of oleic acid in 20.0 gm of octanoic acid; (iii) reaction was at 56° C. with an oxygen flow of 250 mL/min; (iv) the amount of catalyst was 0.40 gm for Na-X Zeolite and 0.050 gm for the sodium acetate; and (v) amounts of pelargonic and azelaic acids were measured in the intermediate time samples as well as at the end. Results are shown in FIGS. 2a and 2b. The performance of the Na-X catalyst according to this invention is again better than that of the sodium acetate soluble catalyst.

After these experiments, 92 w/o of the amount of zeolite catalyst initially added was recovered by simple filtration. In contrast, the sodium acetate can be recovered only with great difficulty, because of the formation of small amounts of soaps during reaction in the presence of this soluble catalyst; these soaps cause residues in later processing that require frequent cleaning of equipment.

EXAMPLE GROUP 3

Materials and processing conditions for these examples were the same as for Example Group 2, except that (i) only half as much of the solution of oleic acid in octanoic acid as in Example Group 2 was used for each test; (ii) the rate of oxygen flow was 134 mL/min; (iii) measurements of product were made only after six hours; (iv) at the end of the first six hour interval, the catalyst was separated by decantation from the reaction product mixture after allowing the catalyst to settle under the influence of gravity, and a fresh batch of the oleic acid ozonide in octanoic acid solution was then added to the separated catalyst and reacted for another six hour interval. This sequence of steps was then repeated twice, so that the same catalyst, to the extent that it could be recovered, was used for four successive six hour intervals of reaction. The w/o of pelargonic and azelaic acids formed in each of these intervals is shown in Table 2. (Because of some loss of catalyst in each step, the results in Table 2 were adjusted by dividing

TABLE 2

| LIFE STUDY OF Na—X ZEOLITE | | | | |
|---|---|---|---|---|
| Interval No.: | 1 | 2 | 3 | 4 |
| w/o Pelargonic Acid | 18.7 | 19.3 | 17.9 | 17.3 |
| w/o Azelaic Acid | 18.4 | 18.1 | 17.5 | 17.2 | the actual measured values for the two acids shown by the fraction of the original amount of catalyst that remained at the beginning of each successive stage.) The results in Table 2 show that there is little if any loss of effectiveness on repeated use of the zeolite catalyst.

EXAMPLE GROUP 4

For these examples, the ozonide was obtained from a commercial scale ozonation plant in which the input starting material is a mixture of 3 parts by weight of technical oleic acid with 1 part by weight of pelargonic acid. (Analysis of the technical oleic acid used in this plant shows 0.42 w/o $C_{12}$ acids, 2.7 w/o $C_{14}$ saturated acids; 0.86 w/o monounsaturated $C_{14}$ acids; 6.3 w/o saturated $C_{16}$ acids; 4.6 w/o monounsaturated $C_{16}$ acids, 0.93 w/o monounsaturated $C_{17}$ acids; 2.8 w/o saturated $C_{18}$ acid; 71.8 w/o monounsaturated $C_{18}$ acids, 8.3 w/o diunsaturated $C_{18}$ acids; and 0.58 w/o triunsaturated $C_{18}$ acids.) Ozonation was performed by means known in the art for large scale plants to produce a product with 1.88 mmole of oxygen-oxygen bonds per gram.

For use in a process according to this invention, the commercial product as described above was diluted with one half its own mass of pelargonic or octanoic acid by mixing with a mechanical stirrer for about 10 min at normal room temperature. This mixture could be used immediately or stored at −20° C. with essentially the same results.

Figure 3:
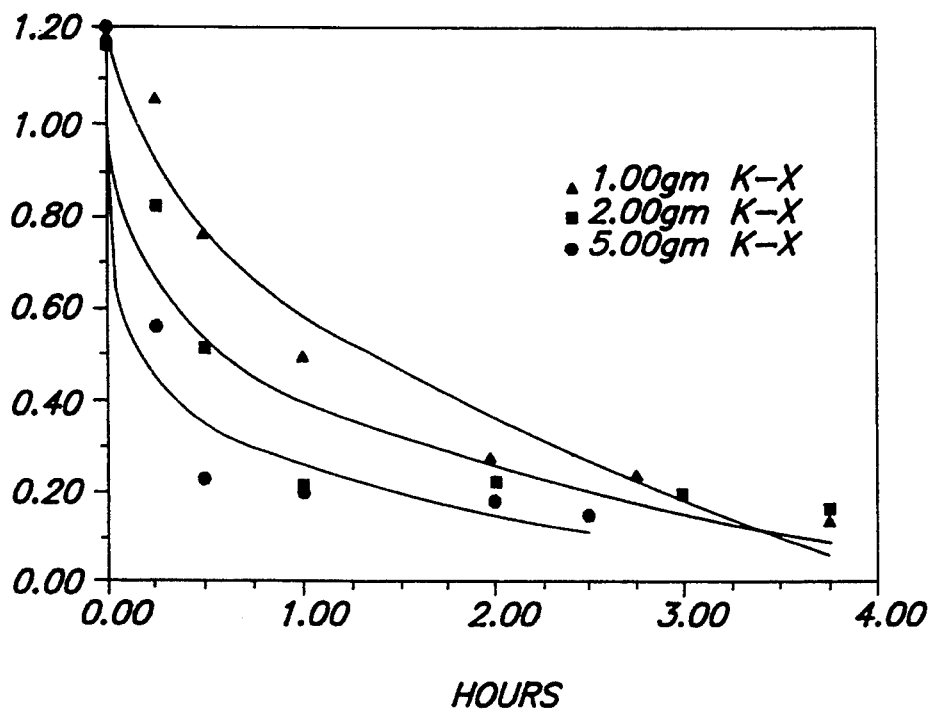

In the first subgroup of these examples, 30 gm of the mixture described above containing oleic ozonide was reacted at 70° C. with a flow of 300 mL/min of diatomic oxygen while in contact with a catalyst of K-X Zeolite (from the same commercial source as for the sodium zeolites) in bead form, with 10 w/o of the beads made up of a binder. The amount of catalyst varied in each specific example, with results shown in FIG. 3.

Figure 4:
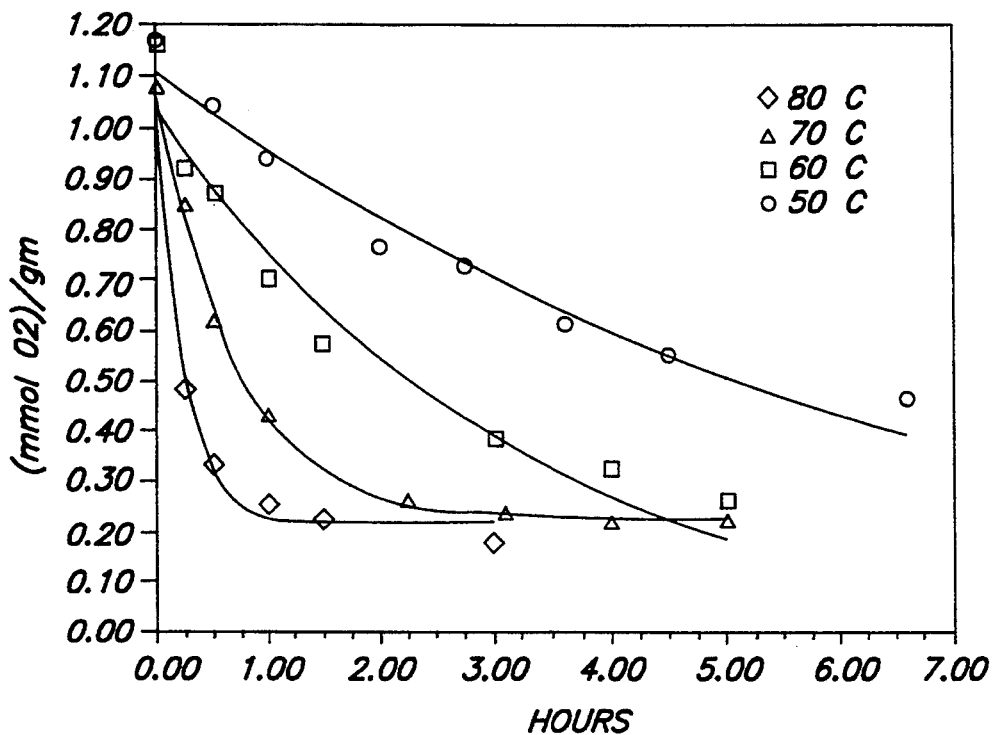

In the second subgroup, the effect of temperature with other variables held constant was studied. For these examples, 60 gm of the mixture described above containing oleic ozonide with one gram of Na-X Zeolite catalyst and an oxygen flow of 300 mL/min was used at the temperature shown in FIG. 4. The other conditions of operation were the same as for Example Group 1. Results are shown in FIG. 4 and Table 3.

TABLE 3

EFFECT OF TEMPERATURE ON PRODUCT DISTRIBUTION IN EXAMPLE GROUP 4, SECOND SUBGROUP

| | w/o of Acid in Product When Reaction is at: | | | |
|---|---|---|---|---|
| Acid Name | 50° C. | 60° C. | 70° C. | 80° C. |
| Pentanoic | 0.532 | 0.338 | 0.314 | 0.225 |
| Hexanoic | 1.653 | 2.036 | 2.505 | 2.301 |
| Heptanoic | 2.104 | 2.230 | 2.684 | 2.494 |
| Octanoic | 1.190 | 1.120 | 1.339 | 1.286 |
| Pelargonic | 53.284 | 51.361 | 58.326 | 53.206 |
| Decanoic | 0.446 | 0.576 | 0.504 | 0.423 |
| Adipic | 0.188 | 0.192 | n.d. | n.d. |
| Pimelic | 0.174 | 0.278 | 0.310 | 0.364 |
| Suberic | 1.036 | 0.214 | 1.125 | 0.299 |
| Azelaic | 14.709 | 18.950 | 17.733 | 19.175 |
| Sebacic | 0.180 | 0.262 | 2.045 | 2.745 |
| Undecandioic | 1.528 | 2.480 | 1.870 | 2.473 |

Notes for Table 3
"n.d." means "not detected".
The "Product" as reported included the pelargonic acid added initially as solvent.

EXAMPLE GROUP 5

Figure 5:
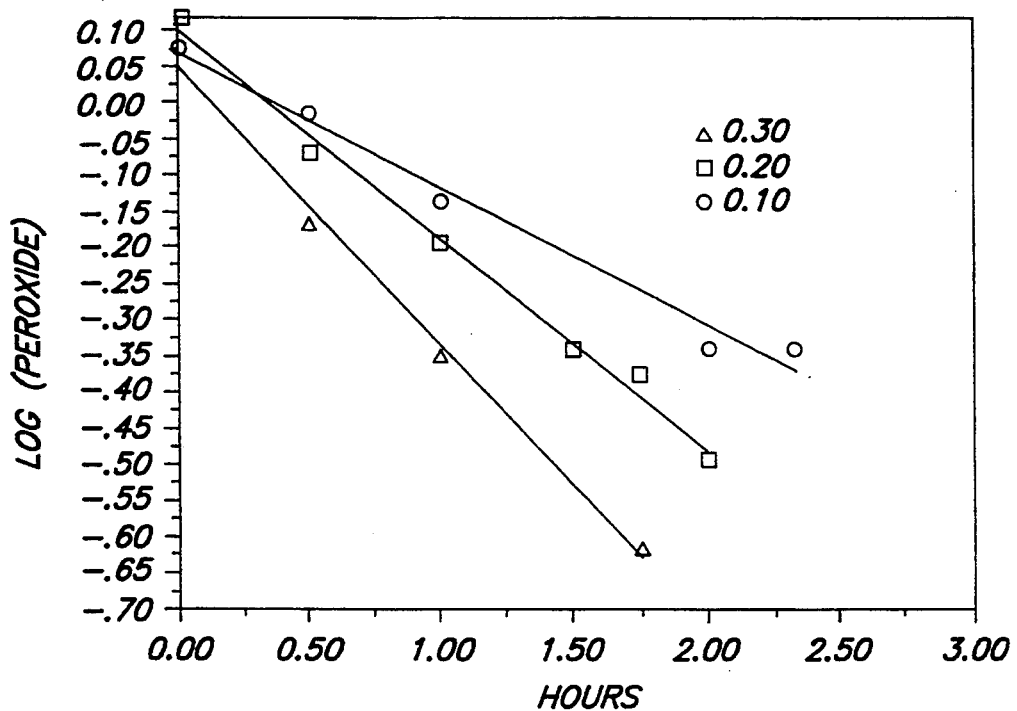

For these examples, all conditions of operation were the same as for the part of Example Group 1 using Na-X Zeolite catalyst, except that (i) the oxygen flow rate was 300 mL/min and (ii) the amount of catalyst was varied as noted in FIG. 5. This Figure shows that a plot of the logarithm of concentration of peroxide remaining against time of reaction is substantially linear, with the slope depending on the amount of catalyst used.

EXAMPLE AND COMPARISON EXAMPLE GROUP 6

This was performed in the same manner as for the parts of Example and Comparison Example Group 1 using Na-X Zeolite catalyst and no catalyst, except that: (i) the amounts of materials used to form the ozonide were 55 grams each of oleic and 2-ethylhexanoic acids; (ii) the ozone-oxygen mixture was supplied for 6 hours at a rate to provide 3 grams per hour of ozone; (iii) a 60 gram batch of the ozonide mixture thus formed with 2 grams of catalyst and a 56 gram batch of the ozonide mixture thus formed with no catalyst were reacted; and (iv) the reaction temperature was 40° C. The concentrations of O—O bonds remaining after various time intervals are shown in Table 4.

TABLE 4

O—O BOND ANALYSIS FOR EXAMPLE GROUP 6

| Hours Reacted | Millimoles of O—O/Gram When Using: | |
|---|---|---|
| | No Catalyst | Na—X Zeolite |
| 0.00 | 1.24 | 1.25 |
| 0.25 | 1.15 | 0.96 |
| 0.50 | 1.22 | 1.03 |
| 1.00 | 1.08 | 0.87 |
| 2.00 | 1.04 | 0.69 |
| 3.00 | 0.95 | |
| 3.50 | | 0.48 |
| 4.50 | 0.77 | |

The values given for oxygen-oxygen single bond (alternatively called "peroxide bond") amounts and for the various mono- and di-carboxylic acids reported in the drawing figures and the tables above were determined by the methods described below.

ANALYSIS OF —O—O— FUNCTIONALITY BY IODOMETRIC TITRATION

Samples of approximately 0.15 to 0.20 g were weighed accurately to three decimal places in a small glass weighing cup and then dropped into a 125 ml iodine flask that was constantly purged with $N_2$. To this was added 10 ml of $CHCl_3$, 2.0 ml of saturated KI and 15 ml of glacial acetic acid. The $N_2$ purge was stopped and the flask immediately stoppered and swirled. The flask was allowed to sit in the dark for 25 minutes and then 50 ml of water was added. The mixture was then titrated with 0.0500M $Na_2S_2O_3$ using a starch indicator. The following formula gives the number of mmoles of —O—O—/gram sample:

$$\frac{\text{mmole —O—O—}}{\text{sample}} = \frac{\text{Volume}_{Na_2S_2O_3} \times 0.0500 \, M_{Na_2S_2O_3}}{2 \times \text{Sample weight}}$$

ANALYSIS OF ACIDS BY GAS LIQUID CHROMATOGRAPHY ("GLC")

Accurately weighed samples of approximately 0.2 g were immediately treated with 2.0 ml of dimethyl sulfide and allowed to stand at room temperature for no less than 3 hours. Afterwards, the excess dimethyl sulfide was removed under vacuum and the remaining oil was heated under reflux in 20.0 ml of 1.0 M HCl/methanol for 1.0 hour. The mixture was then cooled to room temperature and 1.00 ml of 0.0400 gram/ml of dimethyl phthalate in methanol (internal standard) was pipetted into the mixture and a sample was taken for GLC analysis under the following conditions:

Hewlett Packard 5880 Gas Liquid Chromatograph
Column: Chrompack TM WCOT Fused Silica FFAP-CB 25 m×0.33 mm i.d.
Film Thickness 0.28 μm.
Column Flow: 4.0 ml/min He with a 50 ml/min split vent.
Injection Port Temperature: 270° C.
Detector: FID at 300° C. with 30 ml/min. $H_2$ and 350 ml/min. air using 20 ml/min. He for make-up.
Temperature Program: 100° C. for 0.5 min, 12° C./min, 250° C. for 15 min
Representative Compound Retention Times (min): Nonyl Aldehyde (1.93), Methyl Azelaldehydate (6.91), Methyl Pelargonate (2.43), Dimethyl Azelate (7.60).

What is claimed is:

1. A process in which organic molecules containing a structural unit of the formula —HC=CH— are each converted into two or more molecules containing a structural unit of the formula —COOH by reaction with ozone and subsequent or simultaneous reaction with diatomic oxygen gas, wherein the improvement comprises contacting a fluid phase containing ozonides formed by reaction with ozone of the organic molecules containing a structural unit of the formula —HC=CH— with a solid phase catalyst selected from the group consisting of all X and Y type zeolites, during at least part of the reaction with the diatomic oxygen gas.

2. A process according to claim 1, wherein the solid phase catalyst is selected from X type zeolites.

3. A process according to claim 2, wherein the solid phase catalyst is selected from Na-X and K-X type zeolites.

4. A process according to claim 3, wherein the reaction of ozone is carried out at a temperature in the range from about 23° to about 30° C.

5. A process according to claim 2, wherein the reaction of ozone is carried out at a temperature in the range from about 20° to about 40° C.

6. A process according to claim 1, wherein the reaction of ozone is carried out at a temperature in the range from about 17° to about 45° C.

7. A process according to claim 6, wherein the reaction of diatomic oxygen gas with ozonides is carried out at a temperature in the range from about 50° to about 110° C.

8. A process according to claim 5, wherein the reaction of diatomic oxygen gas with ozonides is carried out at a temperature in the range from about 60° to about 90° C.

9. A process according to claim 4, wherein the reaction of diatomic oxygen gas with ozonides is carried out at a temperature in the range from about 60° to about 80° C.

10. A process according to claim 9, wherein the ozone reacted is contained in a gas mixture with an ozone concentration in the range from about 2 to about 6 v/o and the balance of the gas mixture is diatomic oxygen.

11. A process according to claim 8, wherein the ozone reacted is contained in a gas mixture with an ozone concentration in the range from about 1 to about 8 v/o and the balance of the gas mixture is diatomic oxygen.

12. A process according to claim 7, wherein the ozone reacted is contained in a gas mixture with an ozone concentration in the range from about 0.5 to about 14 v/o and the balance of the gas mixture is diatomic oxygen.

13. A process according to claim 6, wherein the ozone reacted is contained in a gas mixture with an ozone concentration in the range from about 0.5 to about 14 v/o and the balance of the gas mixture is diatomic oxygen.

14. A process according to claim 5, wherein the ozone reacted is contained in a gas mixture with an ozone concentration in the range from about 1 to about 8 v/o and the balance of the gas mixture is diatomic oxygen.

15. A process according to claim 4, wherein the ozone reacted is contained in a gas mixture with an ozone concentration in the range from about 2 to about 6 v/o and the balance of the gas mixture is diatomic oxygen.

16. A process according to claim 3, wherein the ozone reacted is contained in a gas mixture with an ozone concentration in the range from about 0.5 to about 14 v/o and the balance of the gas mixture is diatomic oxygen.

17. A process according to claim 2, wherein the ozone reacted is contained in a gas mixture with an ozone concentration in the range from about 0.5 to about 14 v/o and the balance of the gas mixture is diatomic oxygen.

18. A process according to claim 1, wherein the ozone reacted is contained in a gas mixture with an ozone concentration in the range from about 0.5 to about 14 v/o and the balance of the gas mixture is diatomic oxygen.

19. A process according to claim 1 which is performed in separate steps for the reaction of ozone and for the oxidation of the ozonides that were formed during reaction of ozone into carboxylic acids and in which the oxidation of the entire amount of ozonides reacted is carried out in a batch process during which the catalyst is continuously stirred throughout a volume that includes all the ozonides being oxidized, wherein the amount of catalyst used is in the range from about 0.1 to about 50 w/o of the amount of ozonides reacted.

20. A process according to claim 1 which is performed in separate steps for the reaction of ozone and for the oxidation of the ozonides that were formed during reaction of ozone into carboxylic acids and in which the oxidation of the ozonides reacted is carried out continuously by passing a fluid reaction mixture containing the ozonides unidirectionally through a fixed bed containing an amount of catalyst that is in the range from about 1 to about 250 w/o of the amount of the total of ozonides thereof present in the amount of fluid reaction mixture passed through the fixed bed in one hour.

* * * * *